(12) United States Patent
Chun et al.

(10) Patent No.: US 9,239,287 B2
(45) Date of Patent: Jan. 19, 2016

(54) HIGH RESOLUTION OBJECT INSPECTION APPARATUS USING TERAHERTZ WAVE

(75) Inventors: Hyang-Sook Chun, Seoul (KR); Sung-Wook Choi, Suwon (KR); Hyun-Joo Chang, Seoul (KR); Na-Ri Lee, Seoul (KR); Gyeong-Sik Ok, Osan (KR)

(73) Assignee: KOREA FOOD RESEARCH INSTITUTE, Seongnam-si (KR)

( * ) Notice: Subject to any disclaimer, the term of this patent is extended or adjusted under 35 U.S.C. 154(b) by 0 days.

(21) Appl. No.: 14/385,033

(22) PCT Filed: Apr. 10, 2012

(86) PCT No.: PCT/KR2012/002732
§ 371 (c)(1),
(2), (4) Date: Sep. 12, 2014

(87) PCT Pub. No.: WO2013/137513
PCT Pub. Date: Sep. 19, 2013

(65) Prior Publication Data
US 2015/0041658 A1    Feb. 12, 2015

(30) Foreign Application Priority Data
Mar. 14, 2012 (KR) .......... 10-2012-0026046

(51) Int. Cl.
*G01J 5/02* (2006.01)
*G01N 21/3581* (2014.01)
(Continued)

(52) U.S. Cl.
CPC ........ *G01N 21/3581* (2013.01); *G01N 21/8806* (2013.01); *G02B 3/00* (2013.01); *H01Q 15/08* (2013.01); *G01N 2201/06113* (2013.01); *G01N 2201/105* (2013.01)

(58) Field of Classification Search
CPC ................. G01J 5/08; G01N 2/3581
See application file for complete search history.

(56) References Cited

U.S. PATENT DOCUMENTS

2003/0086141 A1* 5/2003 Glaser-Inbari et al. ........ 359/196
2008/0197286 A1* 8/2008 Kasai .................. 250/341.1
2008/0296501 A1  12/2008 Breit et al.

FOREIGN PATENT DOCUMENTS

JP    62-103856 A    5/1987
JP    2003-028799 A  1/2003
(Continued)

OTHER PUBLICATIONS

International Search Report for Application No. PCT/KR2012/002732, mailed Jan. 29, 2013 (4 pages).
(Continued)

*Primary Examiner* — David Porta
*Assistant Examiner* — Hugh H Maupin
(74) *Attorney, Agent, or Firm* — Nutter McClennen & Fish LLP; John J. Penny, Jr.

(57) ABSTRACT

An object inspection apparatus includes a terahertz wave supplying unit for generating a terahertz wave and moving a path of the terahertz wave according to time so that the terahertz wave is supplied to an object to be inspected, a focusing lens located between the terahertz wave supplying unit and the object to be inspected to focus the terahertz wave supplied by the terahertz wave supplying unit, a rotating plate having a plate shape and including a plurality of the focusing lenses with different distances from the center thereof, the rotating plate rotating in the circumferential direction so that one of the focusing lenses is located at a path of the terahertz wave according to the path movement of the terahertz wave, and a terahertz wave detecting unit for collecting and detecting a terahertz wave incident to the object to be inspected.

18 Claims, 11 Drawing Sheets

(51) Int. Cl.
*H01Q 15/08* (2006.01)
*G01N 21/88* (2006.01)
*G02B 3/00* (2006.01)

(56) References Cited

FOREIGN PATENT DOCUMENTS

| JP | 2005-265789 A | 9/2005 |
| KR | 10-1107853 B1 | 1/2012 |
| WO | 2007/067922 A2 | 6/2007 |

OTHER PUBLICATIONS

European Partial Supplementary Search Report for Application No. 12871347.6, issued Sep. 29, 2015 (5 pages).

\* cited by examiner

HIGH RESOLUTION OBJECT INSPECTION APPARATUS USING TERAHERTZ WAVE

TECHNICAL FIELD

The present disclosure relates to an apparatus for inspecting an object, and more particularly, to a nondestructive object inspection apparatus having high detection resolution, which uses a light source in a terahertz wave range, and a focusing lens included in the same.

BACKGROUND ART

Cross-Reference to Related Application

This application claims priority to Korean Patent Application No. 10-2012-0026046 filed in the Republic of Korea on Mar. 14, 2012, the entire contents of which are incorporated herein by reference.

A terahertz wave is an electromagnetic wave located between IR ray and microwave and generally has an oscillation frequency of 0.1 THz to 10 THz.

Although there have been continuous studies conducted on such a terahertz wave, studies have not been satisfactory in comparison to electromagnetic waves in other wavelength bands. Therefore, this wavelength band is also known as a terahertz gap.

However, accompanied with such continuous developments and efforts along with the development of other technical fields such as photon engineering or nano technology, technology of a terahertz wave is being further improved.

Particularly, due to various characteristics such as straightness, penetrability through substances, stability against living bodies, and possibility of quantitative verification, interest towards terahertz is increasing.

For the above reasons, many attempts are being made to apply the terahertz wave in various fields such as a scanning device of an airport or security equipment, a quality inspection device of a food or drug company, a semiconductor inspection device, an inspection device for dental purposes, a gas detection device, an explosion inspection device, a lab-on-a-chip detector or the like.

As described above, many substances are being inspected by using a terahertz wave in various fields in various ways. However, conventional inspection methods using a terahertz wave consume a lot of time and money, and it is difficult to inspect matters with a large area. Moreover, conventional object inspection apparatuses using a terahertz wave have very poor terahertz wave detection resolution.

DISCLOSURE

Technical Problem

The present disclosure is designed to solve the problems of the prior art, and therefore it is an object of the present disclosure to provide an object inspection apparatus which may inspect compositions of an object or impurities by using a terahertz wave and have an improved detection resolution by minimizing a beam spot size when detecting a terahertz wave image.

Other objects and advantages of the present disclosure will be understood from the following descriptions and become apparent by the embodiments of the present disclosure. In addition, it could be understood that the objects and advantages of the present disclosure may be implemented by components defined in the appended claims or their combinations.

Technical Solution

In one aspect, there is provided an object inspection apparatus, which includes: a terahertz wave supplying unit for generating a terahertz wave and moving a path of the terahertz wave according to time so that the terahertz wave is supplied to an object to be inspected; a focusing lens located between the terahertz wave supplying unit and the object to be inspected so that the terahertz wave supplied by the terahertz wave supplying unit is focused; a rotating plate having a plate shape and including a plurality of the focusing lenses with different distances from the center thereof, the rotating plate rotating in the circumferential direction so that one of the focusing lenses is located at a path of the terahertz wave according to the path movement of the terahertz wave; and a terahertz wave detecting unit for collecting and detecting a terahertz wave incident to the object to be inspected.

Preferably, the plurality of focusing lenses included in the rotating plate is arranged in a spiral pattern.

Also preferably, the rotating plate is synchronized as it rotates with the path movement of the terahertz wave.

Also preferably, the focusing lens includes a plurality of circular grooves formed at the rotating plate and having the same center and different radiuses so that the circular grooves are spaced apart from each other by a predetermined distance.

Also preferably, the terahertz wave supplying unit moves the path of the terahertz wave in a straight line.

Also preferably, the terahertz wave supplying unit includes a terahertz wave supplying module for generating and supplying a terahertz wave; a scanning mirror for rapidly reflecting the terahertz wave, supplied by the terahertz wave supplying module, in a predetermined angle range while rotating; and a scanning collimating module for collimating the terahertz wave reflected by the scanning mirror so that the parallel terahertz wave is incident on an object to be inspected.

Also preferably, the object inspection apparatus further includes a display unit for providing an image by using the terahertz wave detected by the terahertz wave detecting unit.

Also preferably, the object inspection apparatus further includes an object transfer unit for transferring the object to be inspected.

In another aspect, there is also provided a focusing lens for focusing a terahertz wave, wherein a plurality of circular grooves having the same center and different radiuses are formed at the focusing lens so that the circular grooves are spaced apart from each other by a predetermined distance.

Advantageous Effects

According to the present disclosure, in a scanning method where terahertz wave supplying locations successively move according to time on a predetermined path, like raster scanning, focusing lenses are located at respective scanning locations so that all terahertz wave beams supplied to an object to be inspected may be focused. Therefore, the object inspection performance using terahertz waves may be improved.

Particularly, in one aspect of the present disclosure, since beams of a smaller size than the wavelength of the terahertz wave may be focused, the terahertz wave scanning image may have an improved resolution in comparison to a conventional image.

In addition, in one aspect of the present disclosure, an image resolution may be improved together while enhancing terahertz wave diffraction efficiency and minimizing losses.

Moreover, in one aspect of the present disclosure, since a ratio of a scanning length to a size of the rotating plate is great, a larger object may be easily scanned.

In addition, in one aspect of the present disclosure, the terahertz wave supplying unit, the rotating plate and the focusing lens may be combined to ensure rapid detection of an image of a large area with high resolution.

The object inspection apparatus according to the present disclosure may be applied to various objects and materials such as foods and semiconductors as an inspection apparatus, and its application is not limited to a specific object.

DESCRIPTION OF DRAWINGS

Other objects and aspects of the present disclosure will become apparent from the following descriptions of the embodiments with reference to the accompanying drawings in which.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the description proposed herein is just a preferable example for the purpose of illustrations only, not intended to limit the scope of the disclosure, so it should be understood that other equivalents and modifications could be made thereto without departing from the spirit and scope of the disclosure.

Figure 1:
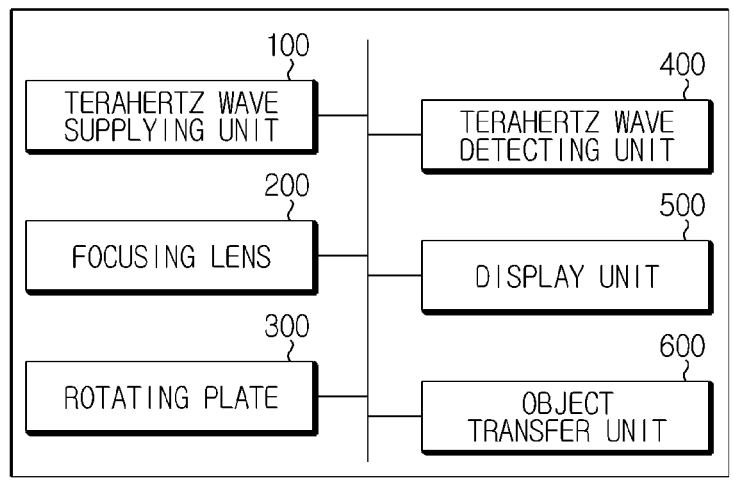
FIG. 1 is a block diagram schematically showing a functional configuration of an object inspection apparatus according to an embodiment of the present disclosure.

FIG. 1 is a block diagram schematically showing a functional configuration of an object inspection apparatus according to an embodiment of the present disclosure. In addition, FIG. 2 is a side sectional view schematically showing an arrangement of the object inspection apparatus using a terahertz wave according to an embodiment of the present disclosure.

Figure 2:
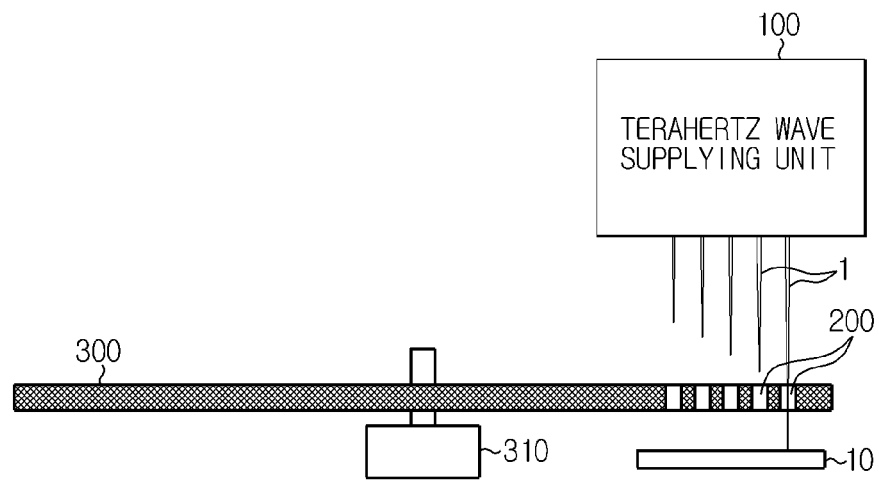
FIG. 2 is a side sectional view schematically showing an arrangement of the object inspection apparatus using a terahertz wave according to an embodiment of the present disclosure.

Referring to FIGS. 1 and 2, the object inspection apparatus according to the present disclosure is a device capable of inspecting an object by using a terahertz wave and includes a terahertz wave supplying unit 100, a focusing lens 200, a rotating plate 300 and a terahertz wave detecting unit 400.

The terahertz wave supplying unit 100 may generate and supply a terahertz wave 1. Here, the terahertz wave 1 represents an electromagnetic wave of a terahertz region, and preferably, may have an oscillation frequency of 0.1 THz to 10 THz. However, even though the oscillation frequency deviates a little from the above range, if the extent is within a level easily conceived by those having ordinary skill in the art of the present disclosure, such a wave may also be recognized as the terahertz wave of the present disclosure.

Particularly, the terahertz wave supplying unit 100 generates a terahertz wave 1 and supplies the terahertz wave 1 to an object to be inspected 10, so that a path of the generated terahertz wave 1 may change according to time. In other words, the terahertz wave supplying unit 100 allows the terahertz waves 1 to be successively supplied to the object to be inspected 10 while changing their paths.

Here, the terahertz wave supplying unit 100 may move the path of the terahertz wave 1 in a straight line. In other words, the terahertz wave supplying unit 100 may scan the terahertz wave 1 in a single axis direction. For example, the terahertz wave supplying unit 100 may allow the terahertz wave 1 to be repeatedly scanned on a straight path of a predetermined distance, like raster scanning.

For instance, as shown in FIG. 2, assuming that the terahertz wave supplying unit 100 generates and supplies five terahertz wave beams 1 in a straight path, the five terahertz wave beams 1 may be generated and supplied successively with a predetermined time difference. However, the number of terahertz wave beams 1 shown in FIG. 2 is just an example, and the number of such terahertz wave beams 1 may be changed in various ways.

As described above, the terahertz wave supplying unit 100 preferably supplies terahertz waves successively, so that the terahertz wave beams become parallel to each other and incident to the object to be inspected 10. For this purpose, the terahertz wave supplying unit 100 preferably allows the parallel terahertz wave beams to be incident to the focusing lens 200 of the rotating plate 300.

The focusing lens 200 may be located between the terahertz wave supplying unit 100 and the object to be inspected 10 so that the terahertz wave supplied by the terahertz wave supplying unit 100 is focused. In other words, the focusing lens 200 may be located on a path of the terahertz wave supplied to the object to be inspected 10 by the terahertz wave supplying unit 100 so that the terahertz wave beams incident to the object to be inspected 10 are focused.

Particularly, the focusing lens 200 according to the present disclosure may focus the terahertz wave supplied by the terahertz wave supplying unit 100 to have a shorter wavelength. Therefore, the object inspection apparatus according to the present disclosure may improve a resolution of a terahertz wave image.

Figure 3:
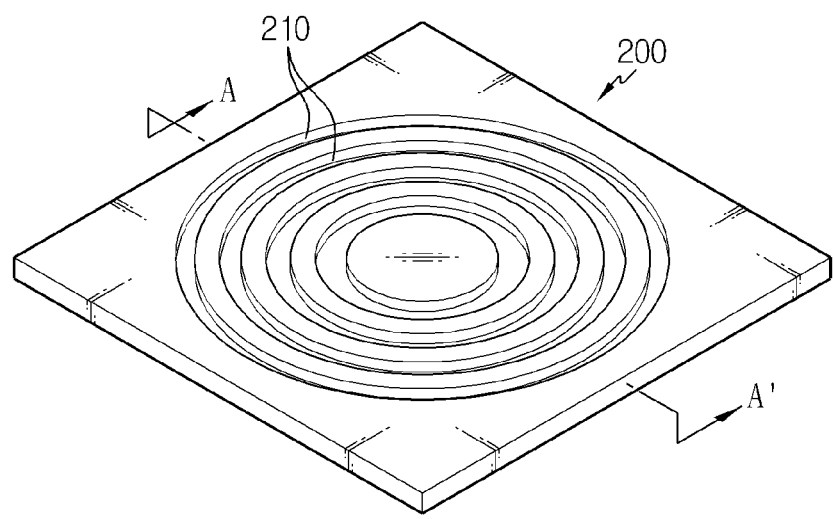
FIG. 3 is a perspective view schematically showing a focusing lens according to an embodiment of the present disclosure.
Figure 4:
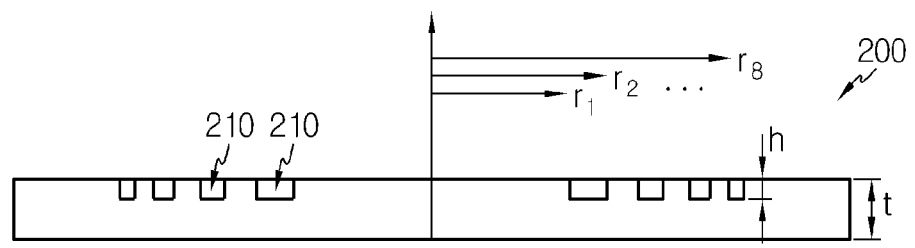
FIG. 4 is a cross-sectional view taken along the line A-A' of FIG. 3.

FIG. 3 is a perspective view schematically showing a focusing lens according to an embodiment of the present disclosure, and FIG. 4 is a cross-sectional view taken along the line A-A' of FIG. 3.

Referring to FIGS. 3 and 4, the focusing lens 200 according to the present disclosure may have a plurality of circular grooves 210 formed in a plate thereof. Here, the plurality of circular grooves 210 may have the same center and different radiuses, and the circular grooves 210 may be spaced apart from each other by a predetermined distance. Therefore, the focusing lens 200 may be shaped so that concave portions where the circular grooves 210 are formed and convex portions where the circular grooves 210 not formed are alternately formed, as shown in FIG. 3.

Particularly, the focusing lens 200 according to the present disclosure may be preferably configured so that the circular grooves 210 are formed with a predetermined depth in the plate made of an optically transparent material for terahertz waves in order to improve the penetration efficiency and ensure efficient beam focusing. According to this configuration, the circular grooves 210 having a predetermined depth with respect to the plate made of a transparent material respectively make predetermined phase differences to incident terahertz wave beams, which eventually induces constructive interference of an evanescent field. Therefore, compared with the case where the plate is made of an opaque material, the diffraction efficiency of the focusing lens 200 is improved, and the loss of terahertz waves may be minimized. For this reason, the terahertz wave focusing effect may be further improved.

At this time, the plurality of circular grooves 210 formed in the focusing lens 200, namely the concave portions, may make the plate have a regularly reduced thickness. In other words, assuming that the focusing lens has a thickness of t in the embodiment of FIG. 4, the circular grooves 210 may have a regular thickness as indicated by h.

Meanwhile, as described above, the focusing lens 200 may be made of an optically transparent material in a terahertz wave region. For example, the focusing lens 200 may be made of PTFE (Poly Tetra Fluoro Ethylene). However, the present disclosure is not limited thereto, and the focusing lens 200 may be made of various materials.

Preferably, the circular grooves 210 formed in the focusing lens 200 may be arranged according to Equation 1 below.

$$r_n = \sqrt{n\lambda f + \frac{n^2 \lambda^2}{4}}$$ Equation 1

Here r represents radiuses of the grooves 210 formed in the focusing lens 200, and n is a natural number and represents an order of the grooves 210 from the center. For more details, referring to FIG. 4, $r_1$ represents a radius of an inner side of the first groove from the center of the focusing lens 200, and $r_2$ represents a radius of an outer side of the first groove. In addition, $r_3$ represents a radius of an inner side of the second groove from the center of the focusing lens 200, and $r_4$ represents a radius of an outer side of the second groove. If $r_n$ is defined as above, in a case where n is an odd number, r represents an inner radius of a circular groove, and in a case where n is an even number, r represents a radius of an outer side of a circular groove.

In other words, $r_n$ may also be regarded as representing a radius of an outer side of a convex portion at the focusing lens 200 and a radius of an outer side of a concave portion. Namely, in FIG. 4, $r_1$ may be regarded as representing a radius of an outer side of the innermost convex portion at the focusing lens 200, $r_2$ may be regarded as representing a radius of an outer side of the next concave portion, and $r_3$ may be regarded as representing a radius of an outer side of the following next concave portion.

In addition, in Equation 1, λ represents a wavelength of the terahertz wave supplied by the terahertz wave supplying unit 100, and f represents a design focal distance of the focusing lens 200.

As described above, if the wavelength of the terahertz wave and the design focal distance are defined, a location of each circular groove at the focusing lens 200 may be determined by using Equation 1.

For example, if the terahertz wave has a wavelength of 0.75 mm and a focal distance of 10 mm, these values may be applied to Equation 1 to obtain $r_n$. As an example, $r_1$ may be calculated as 2.76 mm. Therefore, in this case, the radius of the innermost concave portion in the embodiment of FIGS. 3 and 4 may be 2.76 mm. As another example, $r_8$ may be calculated as 8.31 mm. Therefore, in this case, the radius of an outer side of the outermost groove in the embodiment of FIGS. 3 and 4 may be 8.31 mm.

Meanwhile, even though the embodiment of FIGS. 3 and 4 has been described based on the focusing lens 200 where n=8, namely based on the case where only four circular grooves are formed, the present disclosure is not limited thereto. In other words, n may be set differently, other than n=8. Therefore, the number of circular grooves formed at the focusing lens 200 may be 3 or less or 5 or above.

In addition, even though the embodiment of FIGS. 3 and 4 has been described based on the case where the center portion of the focusing lens 200 has a convex shape (a negative shape), the center portion of the focusing lens 200 may have a concave shape (a positive shape). Therefore, in the embodiment having such a positive shape, $r_n$ may be represented reversely in comparison to the embodiment having a negative shape. For example, $r_1$ may represent a radius of a groove located at the center of the focusing lens 200, and $r_2$ may represent a radius of an outer side of the first convex portion from the center of the focusing lens 200.

As described above, according to the focusing lens 200 according to the embodiment of the present disclosure, the terahertz wave supplied by the terahertz wave supplying unit 100 may be focused.

Figure 5:
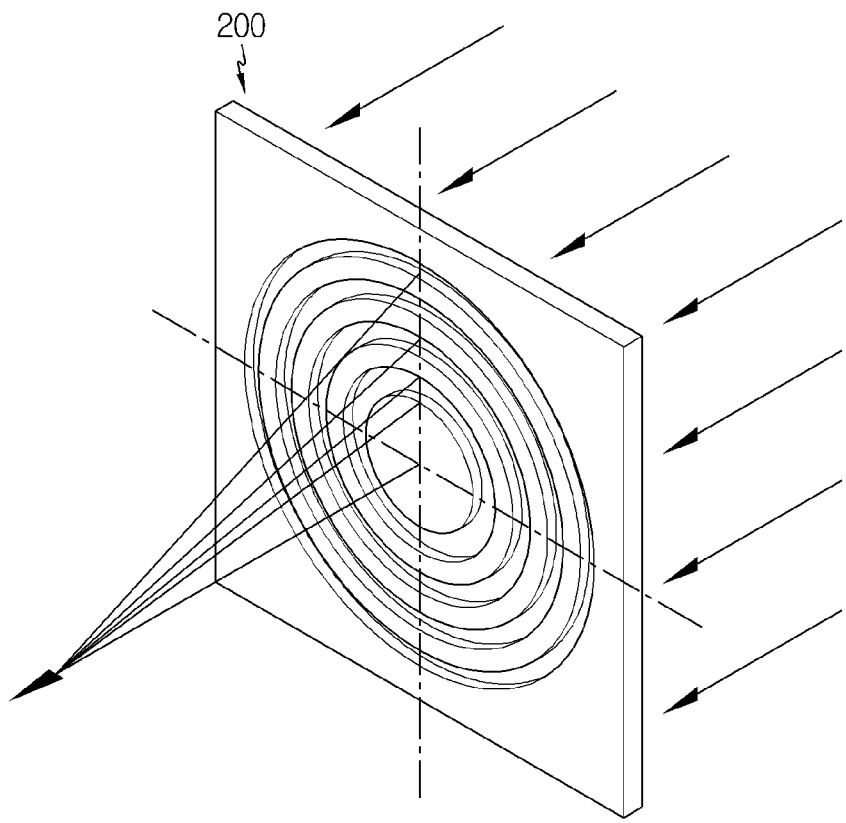
FIG. 5 is a schematic view showing a terahertz wave focused by the focusing lens according to an embodiment of the present disclosure.

FIG. 5 is a schematic view showing a configuration where the terahertz wave is focused by the focusing lens 200 according to the embodiment of the present disclosure.

Referring to FIG. 5, a terahertz wave is supplied to the focusing lens 200 according to the embodiment of the present disclosure, and circular grooves 210 are periodically formed at a surface opposite to the portion where the terahertz wave is supplied. In other words, in FIG. 5, the circular groove 210 is not formed at the rear surface of the focusing lens 200, and the circular grooves 210 are periodically formed at the front surface of the focusing lens 200. In addition, the terahertz wave is incident from the rear surface of the focusing lens 200 and progresses toward the front surface, and is then focused at the front end of the focusing lens 200.

As described above, the grooves 210 of a regular depth are periodically formed at the focusing lens 200 so that the thickness of the focusing lens 200 changes repeatedly, and accordingly the terahertz wave may be focused. This focusing effect may be regarded as being generated due to near field focusing caused by a constructive interference generated by a phase difference and a diffraction effect by an evanescent field generated at the concave and convex portions of the focusing lens 200.

Meanwhile, according to the focusing lens 200 of this embodiment, since the terahertz wave is incident to a surface where the circular groove 210 is not formed and the terahertz wave is focused at the front of a surface where the circular groove 210 is formed, in a case where the focusing lens 200 is applied to FIG. 2, the circular groove 210 may be formed at a lower surface of the focusing lens 200.

Figure 6:
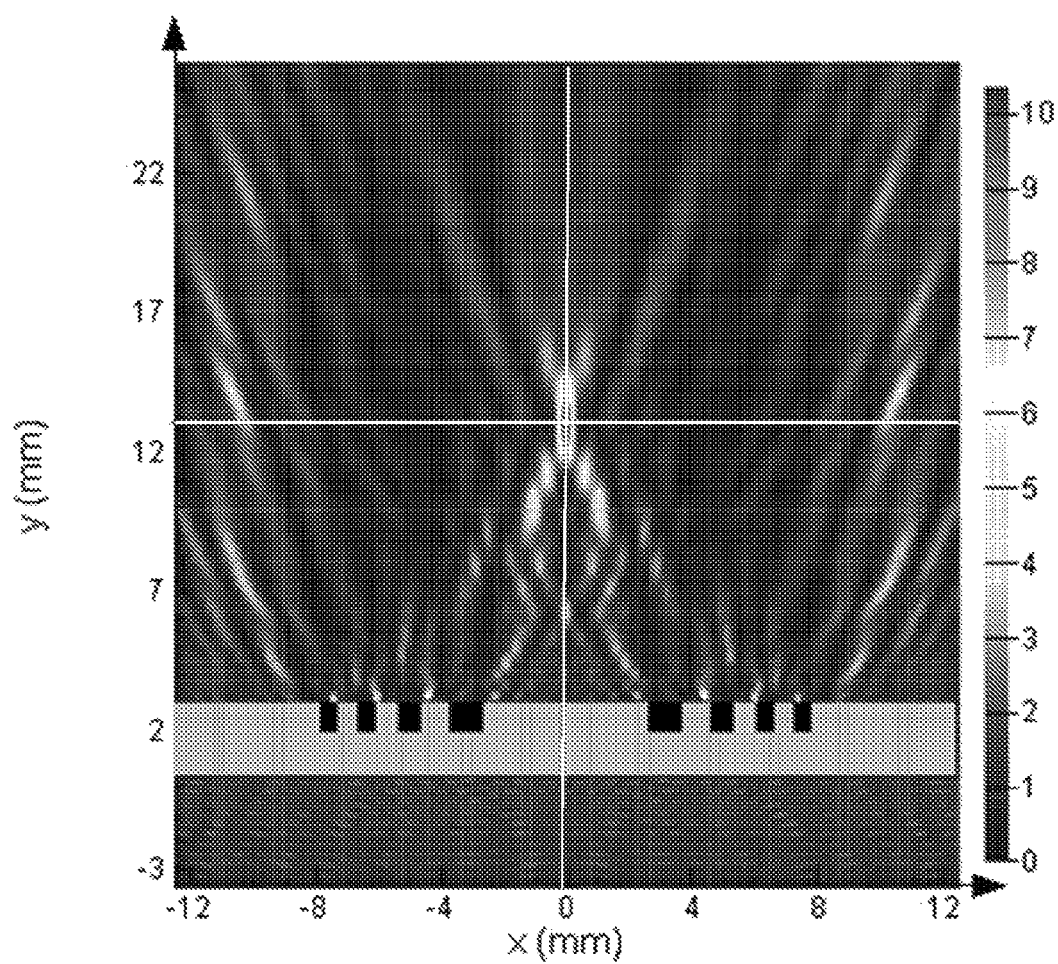
FIG. 6 shows a field intensity distribution of a beam focused by the focusing lens according to an embodiment of the present disclosure.
Figure 7:
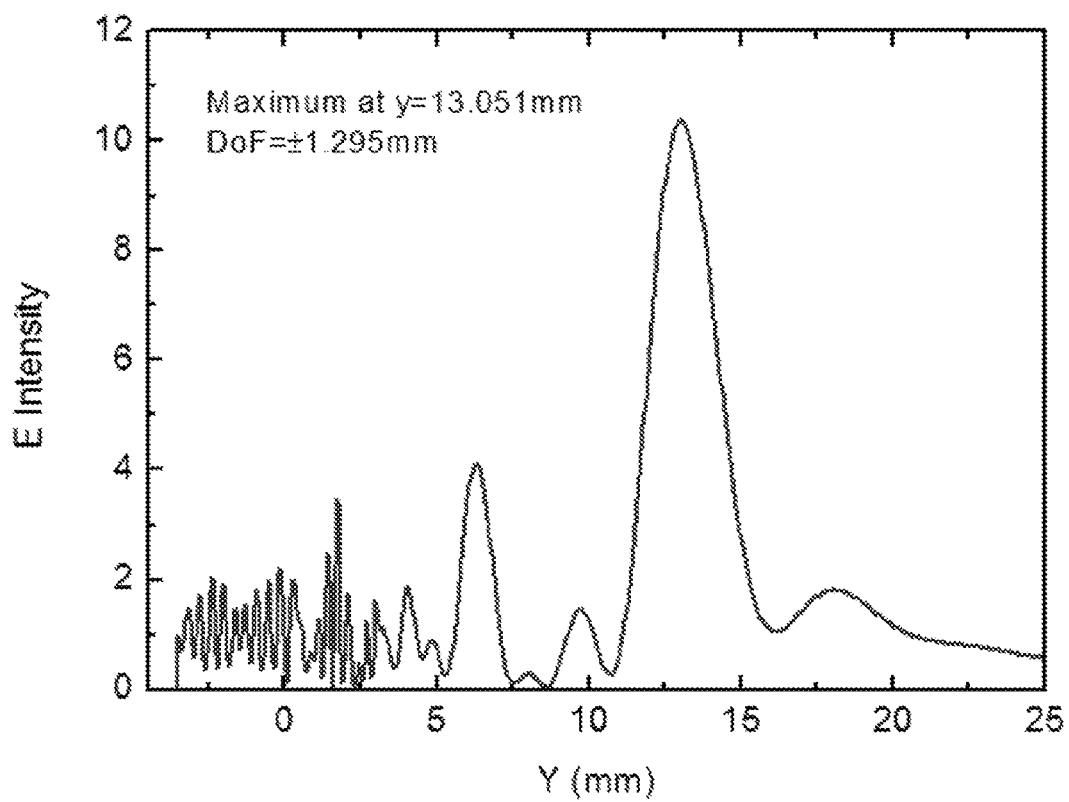
FIGS. 7 and 8 show the field intensity of a central portion of FIG. 6 in x-axis and y-axis directions, respectively.
Figure 8:
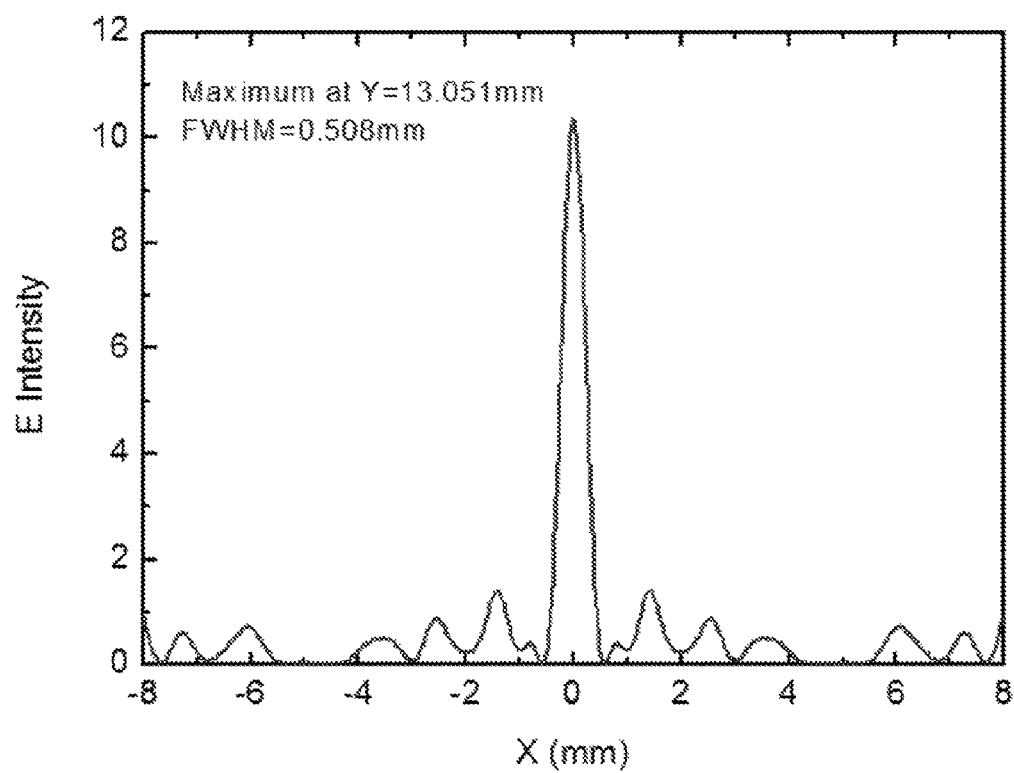

FIG. 6 is a diagram showing a field intensity distribution of a focusing beam by the focusing lens 200 according to the embodiment of the present disclosure, and FIGS. 7 and 8 are diagrams showing the field intensity at the center portion of FIG. 6 in x-axis and y-axis directions, respectively. In more detail, FIGS. 6 to 8 show a 2D finite difference time domain calculation result by using commercial software for the focusing lens 200 according to the embodiment of the present disclosure.

The focusing lens 200 used in FIGS. 6 to 8 has a thickness of 2.5 mm, and the groove 210 has a depth of 1 mm and is made of PTFE material. In addition, the used terahertz wave has a wavelength of 0.75 mm and a design focal distance of 10 mm. In addition, the focusing lens 200 has a negative shape and has four circular grooves 210 so that n will be 8. At this time, the radius of the circular groove 210 formed at the focusing lens 200, namely $r_n$, is calculated according to Equation 1. For example, $r_1$ is 2.76 mm, and $r_8$ is 8.31 mm.

First, referring to FIG. 6, it could be understood that a terahertz wave is well focused when the terahertz wave is supplied to the focusing lens 200 according to the embodiment of the present disclosure. Namely, if a terahertz wave is supplied at the lower end of the focusing lens 200 in FIG. 6, the supplied terahertz wave may be focused as indicated by points at a crossing portion when passing through the focusing lens 200. At this time, the focused terahertz wave has a focal distance of 9.8 mm, which is very close to the design focal distance which is 10 mm.

Next, referring to FIGS. 7 and 8, the field intensity of the center portion with respect to the result of FIG. 6 is shown in x-axis and y-axis directions, and a DoF (Depth of Focus) and a FWHM (Full Width of Half Maximum) size may be calculated based on the above result.

Particularly, in the result of FIG. 8, the terahertz wave beam focused by the focusing lens 200 shows a FWHM of 0.508 mm. This FWHM is as low as being substantially close to a half of 0.75 mm which is the wavelength of the used terahertz wave beam. Therefore, it could be understood that the focusing lens 200 according to the embodiment of the present disclosure may focus the terahertz waves to have a shorter wavelength.

As described above, according to the embodiment of the present disclosure, each terahertz wave beam may be focused, particularly below a specific wavelength, through the focusing lens 200. However, the terahertz waves supplied by the terahertz wave supplying unit 100 change their paths successively according to time, like the raster scanning method. Therefore, as the terahertz waves change their paths according to time as described above, the focusing lens 200 may also be positioned so that all scanned terahertz wave beams are capable of focusing. This may be accomplished by the rotating plate 300 described below.

The rotating plate 300 may have a plate shape such as a disk shape and have a plurality of focusing lenses 200. In addition, the plurality of focusing lenses 200 provided at the rotating plate 300 may be arranged to have different distances from the center of the rotating plate 300.

Figure 9:
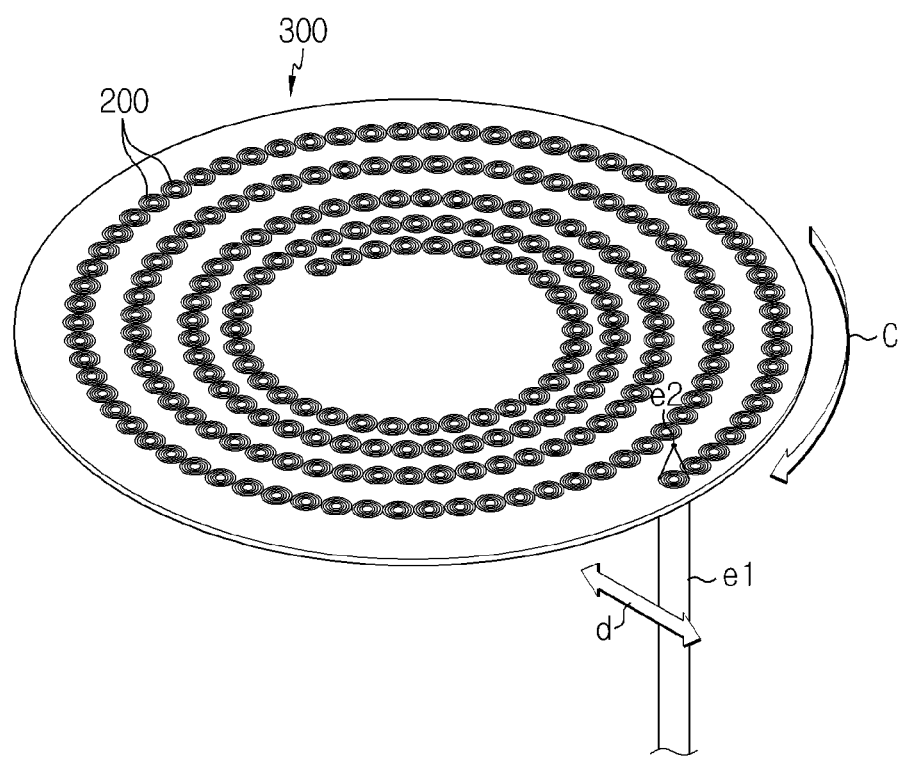
FIG. 9 is a perspective view schematically showing a rotating plate having a plurality of focusing lenses according to an embodiment of the present disclosure.

FIG. 9 is a perspective view schematically showing the rotating plate 300 including a plurality of focusing lenses 200 according to the embodiment of the present disclosure.

Referring to FIG. 9, the rotating plate 300 according to the embodiment of the present disclosure may include a plurality of focusing lenses 200 having different distances from the center of the rotating plate 300. In addition, each focusing lens 200 may focus each terahertz wave beams successively supplied to an object to be inspected 10, while changing their paths.

The rotating plate 300 may rotate in the circumferential direction by means of a rotor 310 or the like, as shown in FIG. 2. In addition, by rotating, the rotating plate 300 may allow any one focusing lens 200 to be located at a path of the terahertz wave according to a path movement of the terahertz wave. For example, the terahertz wave supplying unit 100 may move a path of the terahertz wave by successively scanning terahertz waves in a straight path, as indicated by the arrow d in FIG. 9. At this time, the rotating plate 300 may correspond to the path movement of the terahertz wave by rotating in the circumferential direction as indicated by the arrow c in FIG. 9. In other words, with respect to terahertz waves successively supplied while changing their paths, the rotating plate 300 may allow different focusing lenses 200 to be successively located at the paths of the terahertz waves by rotating.

According to this embodiment, according to the path movement of the terahertz wave, different focusing lenses 200 are successively placed on the path of the terahertz wave. Therefore, as shown in FIG. 9, the terahertz wave beam indicated by e1 may be focused as indicated by e2 by passing through the focusing lens 200 of the rotating plate 300.

For this purpose, the rotation of the rotating plate 300 is preferably synchronized with the path movement of the terahertz wave. In other words, the rotating plate 300 preferably synchronizes the rotating speed or the like with a terahertz wave scanning speed so that the focusing lens 200 is located on a path of the terahertz wave according to a terahertz wave scanning location of the terahertz wave supplying unit 100. In this case, a sensor such as an encoder may be attached to the rotor 310 connected to the rotary shaft of the rotating plate 300, and the focusing lens 200 of the rotating plate 300 may be synchronized with the terahertz wave scanning location by means of the rotor 310.

As described above, the plurality of focusing lenses 200 are preferably arranged in a spiral pattern at the rotating plate 300 as shown in FIG. 9, so that different focusing lenses 200 are located according to the path movement of the terahertz wave as the rotating plate 300 is rotating.

Figure 10:
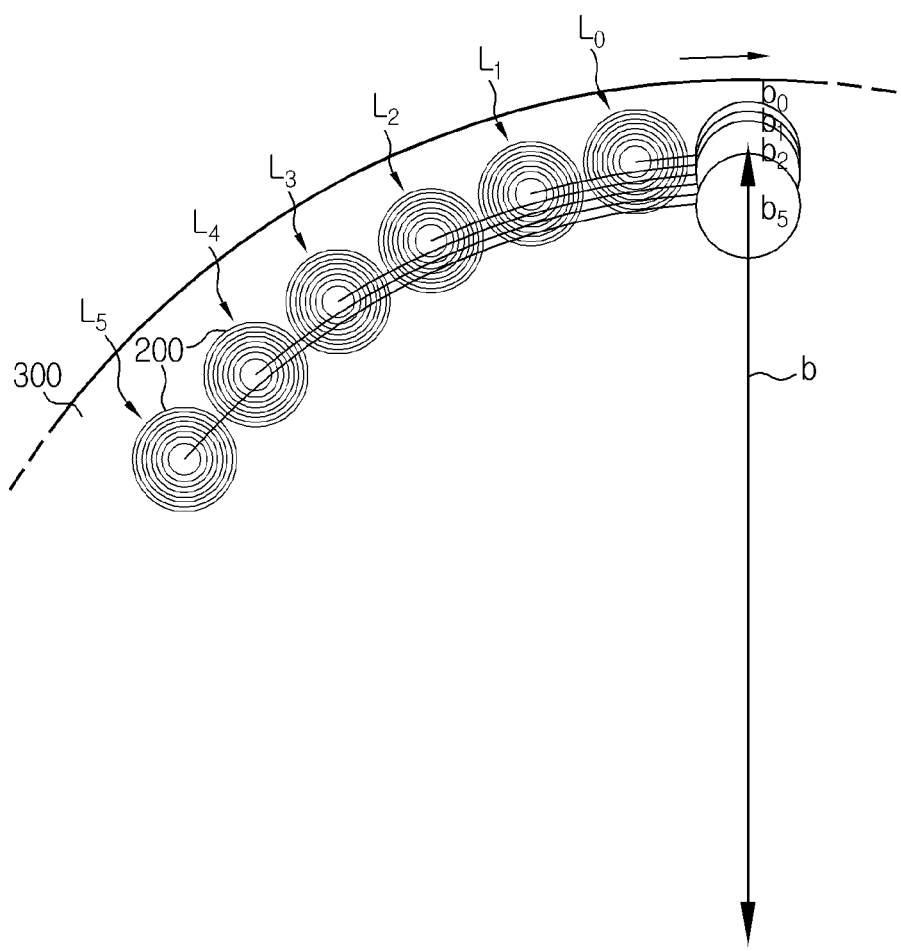
FIG. 10 is a schematic view showing a configuration where the path movement of a path movement is synchronized with the rotation of the rotating plate according to an embodiment of the present disclosure.

FIG. 10 is a schematic view showing a configuration where the path movement of the terahertz wave according to the embodiment of the present disclosure is synchronized with the rotation of the rotating plate 300. In FIG. 10, the rotating plate 300 and the focusing lens 200 are just partially depicted for convenience.

Referring to FIG. 10, the terahertz wave supplying unit 100 may successively supply terahertz wave beams while periodically reciprocating along a predetermined straight line connecting through the outermost circumference and the center of the rotating plate 300 as indicated by the arrow b. However, the scanning path of the terahertz wave supplying unit 100 may be formed in a region between a location corresponding to the outermost focusing lens 200 of the rotating plate 300 and a location corresponding to the innermost focusing lens 200. This is because the focusing lens 200 may not be formed at the center portion of the rotating plate 300.

In the rotating plate 300 of FIG. 10, several focusing lenses 200 are provided, and only six focusing lenses $L_0$ to $L_5$ are depicted in FIG. 10. In addition, the distances from the centers of the focusing lenses 200 to the center of the rotating plate 300 may be different from each other.

First, when a terahertz wave beam is supplied, namely scanned, to a location $b_0$ by the terahertz wave supplying unit 100, the focusing lens 200 $L_0$ may move to the location $b_0$ so that the terahertz wave beam may pass through the focusing lens 200 $L_0$. Next, when the terahertz wave beam moves its path to be scanned to the location $b_1$, the rotating plate 300 may rotate in a clockwise direction so that the focusing lens $L_1$ moves to the location $b_1$. Then, the terahertz wave beam scanned at the location $b_1$ may be focused through the focusing lens $L_1$. Next, when the terahertz wave beam changes its path to be scanned to the location $b_2$, the rotating plate 300 may further rotate in a clockwise direction so that the focusing lens $L_2$ may move to the location $b_2$. Therefore, the terahertz wave beam supplied at the location $b_2$ may pass through the focusing lens $L_2$. When the terahertz wave beams are successively scanned while changing their paths to the locations $b_3$, $b_4$ and $b_5$ as described above, the rotating plate 300 may rotate in a clockwise direction so that the focusing lenses $L_3$, $L_4$ and $L_5$ are located at the locations $b_3$, $b_4$ and $b_5$ to focus the terahertz wave beam scanned at the corresponding locations.

The embodiment of FIG. 10 depicts that the circular groove 210 of the focusing lens 200 is formed at the front surface of the rotating plate 300, and so the terahertz wave beam may be regarded as being supplied from the rear surface of the rotating plate 300 toward the front surface thereof.

Meanwhile, even though only $b_1$ to $b_5$ are depicted in the figures as terahertz wave beam scanning locations, the terahertz wave beam may be continuously supplied toward the center of the rotating plate 300 in addition to the above. In addition, regarding the terahertz wave supplied as above, different focusing lenses 200 having shorter distances than $L_5$ from the center portion of the rotating plate 300 successively correspond to terahertz wave beam locations, respectively, by the rotation of the rotating plate 300, so that all terahertz wave beams scanned along different paths may be focused.

For example, assuming that the subsequent terahertz wave beam scanning locations of the terahertz wave supplying unit 100 are $b_0$ to $b_{300}$ along the arrow b, at least focusing lens 200 $L_0$ to $L_{300}$ corresponding to $b_0$ to $b_{300}$ are preferably present at the rotating plate 300. At this time, $L_0$ may represent the outermost focusing lens 200 at the rotating plate 300, and $L_{300}$ may represent the innermost focusing lens 200. In this embodiment, the terahertz wave beam may be supplied from the location $b_0$ in the order of locations $b_0$, $b_1$, $b_2$, . . . , $b_{299}$, $b_{300}$ successively. In this case, the rotating plate 300 may allow the focusing lens $L_0$, $L_1$, $L_2$, . . . , $L_{299}$, $L_{300}$ to be successively placed at locations $b_0$, $b_1$, $b_2$, . . . , $b_{299}$, $b_{300}$, respectively, by means of rotation. After that, the terahertz wave beam may be supplied again in the order of $b_0$, $b_1$, $b_2$, . . . , and in this case, the rotating plate 300 may allow $L_0$, $L_1$, $L_2$, . . . to be placed again at locations $b_0$, $b_1$, $b_2$, . . . by means of rotation.

As described above, if the rotation of the rotating plate 300 is synchronized with the path movement of the terahertz wave, namely the terahertz wave scanning locations, all terahertz wave beams whose paths have moved may pass through the focusing lens 200. Therefore, even though terahertz waves are successively supplied while moving their paths, the entirely focused terahertz wave may be supplied to the object to be inspected 10.

As described above, the terahertz wave supplying unit 100 may allow terahertz waves to be supplied while periodically moving on a predetermined path, for example on a straight path, and the rotating plate 300 may rotate while being synchronized with the path movement of the terahertz wave. For this purpose, at the rotating plate 300, the focusing lenses 200 are preferably arranged in a spiral pattern. Hereinafter, the arrangement of the focusing lenses 200 will be described in more detail.

Figure 11:
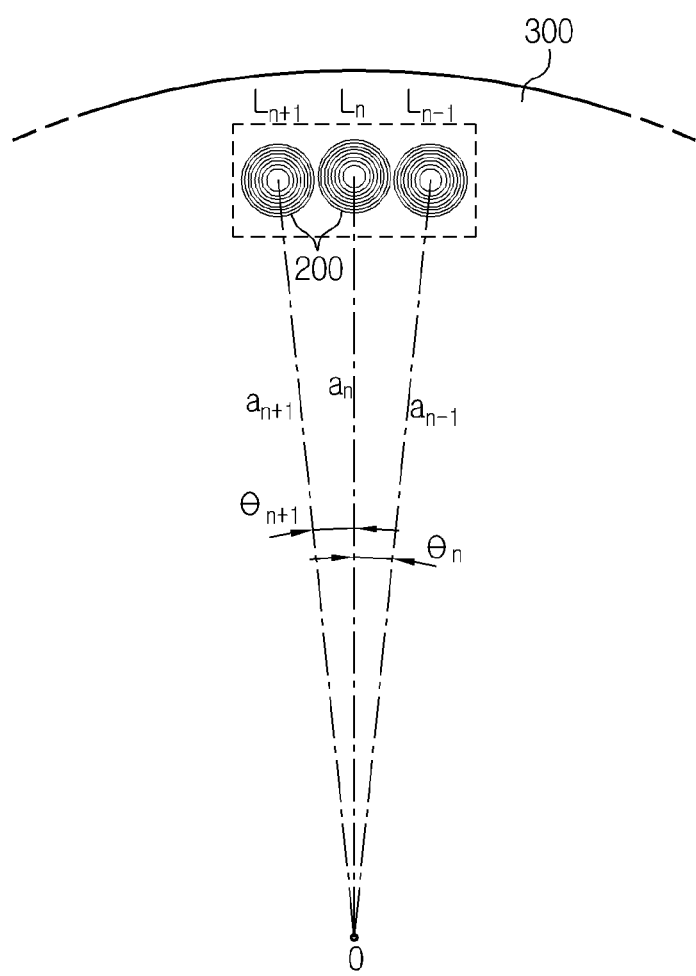
FIG. 11 is a diagram showing an arrangement of some focusing lens provided at the rotating plate.
Figure 12:
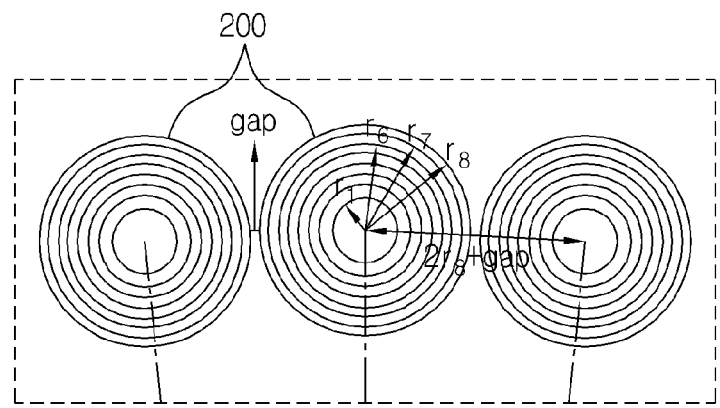
FIG. 12 is an enlarged diagram showing only a portion of the focusing lens in FIG. 11.

FIG. 11 shows an arrangement of some focusing lenses 200 provided at the rotating plate 300, and FIG. 12 is a partially enlarged view showing only the focusing lenses 200 of FIG. 11. In FIGS. 11 and 12, only three focusing lenses 200 are depicted for convenience.

Referring to FIGS. 11 and 12, three focusing lenses 200 of $L_{n+1}$, $L_n$ and $L_{n-1}$ are successively arranged in the circumferential direction of the rotating plate 300, and the distance of each focusing lens 200 from the center O of the rotating plate 300 is represented by $a_{n+1}$, $a_n$ and $a_{n-1}$. In addition, $r_1$ to $r_8$ represent a distance from the center of each focusing lens 200 to the circular groove 210 as described above, and a gap between the focusing lenses 200 is represented by a gap.

At this time, an angle $\theta_n$ between center lines connecting the centers of the focusing lenses 200 and the center of the rotating plate 300 may be calculated by means of trigonometry according to Equation 2 below:

$$\theta_n = a\cos\left(\frac{a_n^2 + a_{n-1}^2 - (2r_8 + \text{gap})^2}{2a_n a_{n-1}}\right), (n = 1, 2, \ldots)\quad \text{Equation 2}$$

Here, a distance $a_n$ from each focusing lens 200 to the center of the rotating plate 300 is preferably as small as a minimal image resolution. In other words, $a_{n-1}$-$a_n$ is preferably in the level of a minimal image resolution. For example, assuming that a beam obtained by focusing terahertz wave of 0.4 THz (with a wavelength of 0.75 mm) has a size of about 0.5 mm as in the embodiment of FIGS. 6 to 8, a detectable minimal image resolution will be about 0.5 mm. Therefore, in this case, $a_n$ may be set to be smaller than $a_{n-1}$ by about 0.5 mm.

In addition, if $a_{n-1}$ is determined as above, the value of $a_{n-1}$ and the predetermined value of $a_n$ may be applied to Equation 2 together with $r_8$ and the gap to determine $\theta_n$.

However, the distance $a_0$ from the outermost focusing lens 200 of the rotating plate 300 to the center of the rotating plate 300 may be arbitrarily determined as an optimal value.

The focusing lenses 200 may be arranged at the rotating plate 300 while gradually decreasing the distance $a_n$ from the rotating plate 300 to its center, and may converge toward the center of the rotating plate 300. In addition, the focusing lenses 200 may be arranged continuously as described above unless the focusing lenses 200 overlap each other.

If the focusing lenses 200 are arranged as above at the rotating plate 300, the focusing lenses 200 may be eventually arranged in a spiral pattern as shown in FIG. 9. Particularly, according to the embodiment of the present disclosure, at the rotating plate 300, the arrangement of the focusing lenses 200 may have several turns, without being limited to just one turn. In other words, the spiral arrangement of the focusing lenses 200 may have two or more turns at the rotating plate 300.

According to this embodiment, compared with the case where the spiral arrangement has a single turn, the focusing lenses 200 may be located at the path movement of longer terahertz wave beams. In other words, if the spiral arrangement of the focusing lenses 200 has several turns, the terahertz wave scanning location may be changed in a longer region in comparison to the case where the spiral arrangement has a single turn. Therefore, according to this embodiment, a wider area may be scanned.

In more detail, assuming that a terahertz wave of 0.4 THz is scanned on a straight path, $a_0=190$ mm, gap=0.5 mm, the rotating plate 300 has a radius of 205 mm, each focusing lens 200 has four circular grooves 210, and scanning is performed with 0.5 mm resolution, if the focusing lenses 200 are arranged according to Equation 2, 215 focusing lenses 200 may be arranged at most without overlapping each other. In addition, the arrangement of the focusing lenses 200 may have a pattern as shown in FIG. 9. In other words, 215 focusing lenses 200 may be arranged at the rotating plate 300 in a spiral pattern, and this spiral arrangement may have five turns.

According to this embodiment, a terahertz wave scanning distance may be about 107 mm. In other words, since the distance $a_0$ from the center of the rotating plate 300 to the center of the outermost focusing lens 200 is 190 mm and the distance $a_{214}$ from the center of the rotating plate 300 to the center of the innermost focusing lens 200 is 93 mm, the straight scanning distance of the object inspection apparatus according to this embodiment may be 107 mm, which is obtained by subtracting 93 mm from 190 mm.

Meanwhile, the pattern of the focusing lens 200 provided at the rotating plate 300 may be implemented in various ways. In other words, the focusing lens 200 may be implemented in various ways at the rotating plate 300. For example, the focusing lens 200 may be provided at the rotating plate 300 to be integrated with the rotating plate 300. In this case, the focusing lens 200 may be provided by forming the circular groove 210 at one surface of a plate of the rotating plate 300, or the focusing lens 200 may be formed in the stage of manufacturing the rotating plate 300. At this time, the rotating plate 300 may be made of the same material as the focusing lens 200. For example, the rotating plate 300 may be made of an optically transparent material for terahertz waves together with the focusing lens 200. As another example, the focusing lens 200 may be provided at the rotating plate 300 to be separated from the rotating plate 300. In this case, a hole is formed at the rotating plate 300 to be coupled with the focusing lens 200, and the focusing lens 200 is inserted into the hole so that the focusing lens 200 is provided at the rotating plate 300. In addition, the focusing lens 200 may be provided to the rotating plate 300 in various ways.

The terahertz wave detecting unit 400 collects and detects a terahertz wave which is supplied by the terahertz wave supplying unit 100 and is incident to the object to be inspected 10 through the focusing lens 200. Particularly, since the terahertz wave incident to the object to be inspected 10 according to the present disclosure may be focused to have a shorter wavelength by the focusing lens 200, the resolution of an image detected by the terahertz wave detecting unit 400 may be greatly improved.

As described above, according to the present disclosure, the terahertz wave supplying unit 100 may scan terahertz waves while moving their paths successively according to time like the raster scanning method, so that different focusing lenses 200 are located respectively at terahertz wave scanning locations by the movement of the rotating plate 300. Therefore, all terahertz waves supplied while moving their paths are supplied through the focusing lens 200 to the object to be inspected 10, and as a result the focused terahertz waves are supplied to the object to be inspected 10. For this, the location of the object to be inspected 10 is preferably near a focal distance of the focusing lens 200 provided at the rotating plate 300.

Particularly, since the focusing lens 200 according to the embodiment of the present disclosure may be focused to have a shorter wavelength with respect to the terahertz waves, the resolution of the detected image may be greatly improved.

Meanwhile, as described above, the terahertz wave supplying unit 100 scans terahertz waves while moving their paths according to time, and for this, the terahertz wave supplying unit 100 may be implemented in various ways.

Figure 13:
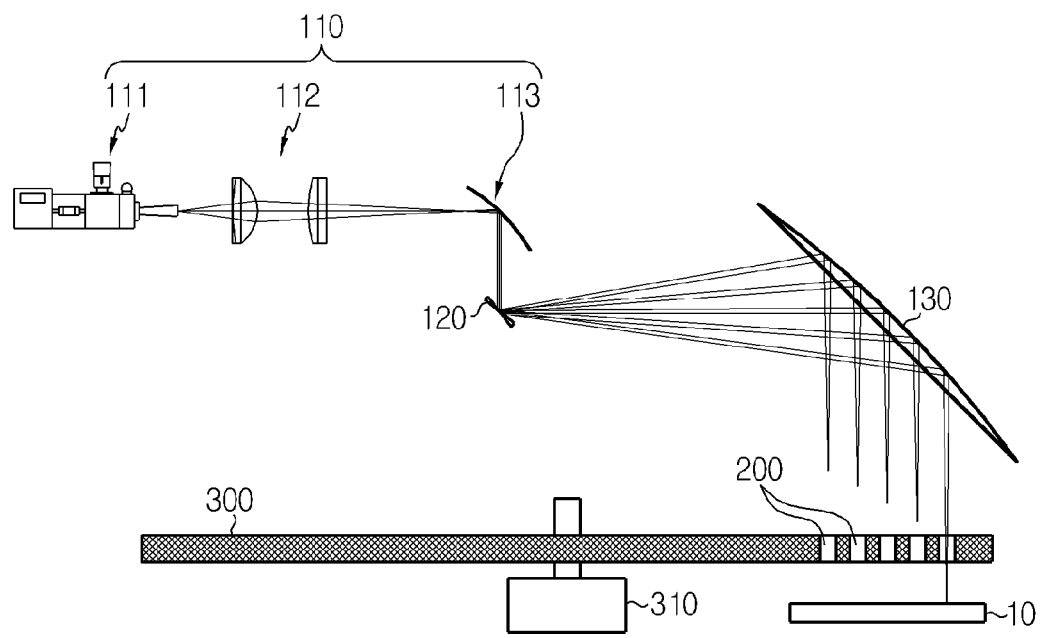
FIG. 13 is a schematic view showing a configuration of an object inspection apparatus including a terahertz wave supplying unit according to an embodiment of the present disclosure.

FIG. 13 is a schematic view showing an object inspection apparatus including the terahertz wave supplying unit 100 according to an embodiment of the present disclosure.

As shown in FIG. 13, the terahertz wave supplying unit 100 according to the present disclosure may include a terahertz wave supplying module 110, a scanning mirror 120 and a scanning collimating module 130.

The terahertz wave supplying module 110 is an element which generates and supplies a terahertz wave. The terahertz wave supplying module 110 may be implemented in various ways to generate and supply a terahertz wave.

Preferably, the terahertz wave supplying module 110 may include a terahertz wave generating unit 111, an optical focusing unit 112 and a beam collimating unit 113.

The terahertz wave generating unit 111 generates a terahertz wave and emits the generated terahertz wave to the optical focusing unit 112.

Preferably, the terahertz wave generating unit 111 may be implemented using a Gunn diode. The Gunn diode is a diode which oscillates an electromagnetic wave by using a Gunn Effect and has advantages such as low price and minimized volume. The terahertz wave generating unit 111 of the present disclosure may generate a terahertz wave by using the Gunn diode. In this case, the terahertz wave generated by the Gunn diode may be emitted through a horn. However, the present disclosure is not limited to just a Gunn diode, and the terahertz wave generating unit 111 may be implemented in various ways.

The optical focusing unit 112 may collimate terahertz waves emitted by the terahertz wave generating unit 111 to have a reduced field angle. In other words, if terahertz waves are generated and emitted by a Gunn diode or the like, the emitted terahertz waves are incident to the optical focusing unit 112, and the optical focusing unit 112 reduces a field angle of the incident light, namely the incident terahertz wave, so that the terahertz wave with the reduced field angle is directed to the beam collimating unit 113. At this time, the optical focusing unit 112 may be set to have different magnifications at its input and output portions.

Preferably, the optical focusing unit 112 may be implemented using aspheric lens, as shown in FIG. 13. Particularly, in a case where lens with an aspheric surface is used for the optical focusing unit 112 to reduce the field angle of light, the spherical value may be minimized. If the aspheric lens is used for the optical focusing unit 112, the flat portion is preferably oriented toward the outer side as shown in FIG. 13.

Meanwhile, the optical focusing unit 112 preferably has a regular refractive index in a terahertz wave region and a visible ray region and allows easy lens alignment. Therefore, the optical focusing unit 112 may be made of TPX polymer (polymethyl pentene). TPX is transparent in a wavelength of 633 nm and has a refractive index of 1.46, which is similar to the refractive index of the terahertz wave region. Therefore, the lens of the optical focusing unit 112 is preferably made of a TPX polymer material. However, the present disclosure is not limited thereto, and the lens of the optical focusing unit 112 may also be made of various materials other than TPX polymer.

The beam collimating unit 113 collimates the terahertz waves focused by the optical focusing unit 112. Therefore, the terahertz waves passing through the optical focusing unit 112 are focused at the focal point and then reflected parallel by the beam collimating unit 113, and the reflected terahertz waves are oriented toward the scanning mirror 120.

Preferably, the beam collimating unit 113 may be implemented using a parabolic reflector. Particularly, the parabolic reflector of the beam collimating unit 113 may have an off-axis paraboloid. In a case where the beam collimating unit 113 is implemented using an off-axis paraboloid as described above, the beam spot size of the terahertz wave incident to the focusing lens 200 of the rotating plate 300 may be adjusted by varying the distance between the focus of the parabolic reflector and the focus of the lens located at the rear side of the optical focusing unit 112.

Meanwhile, in this embodiment, even though it has been illustrated that the terahertz wave supplying module 110 includes the terahertz wave generating unit 111, the optical focusing unit 112 and the beam collimating unit 113, it is just an example, and the terahertz wave supplying module 110 may be implemented in various ways.

For example, the terahertz wave supplying module 110 may be implemented with QCL (Quantum Cascade Laser) or a far infrared laser. Such QCL or far infrared laser is a consecutive oscillation laser which may consecutively oscillate laser. For example, the QCL is an electromagnetic wave emitting laser using a shift between sub-bands formed with a quantum well structure, different from a general laser using a semiconductor band gap shift. The QCL does not use electron-hole recombination but uses a shift of only electrons, and so the QCL may consecutively emit laser step by step by using the repeatedly formed quantum well structure.

Meanwhile, the terahertz wave supplied by the terahertz wave supplying module 110 including the terahertz wave generating unit 111, the optical focusing unit 112 and the beam collimating unit 113 may be incident to the scanning mirror 120, then reflected to the scanning collimating module 130, focused by the focusing lens 200 of the rotating plate 300, and then incident to the object to be inspected 10.

The scanning mirror 120 rapidly reflects the terahertz wave supplied by the terahertz wave supplying module 110. At this time, the scanning mirror 120 may rapidly rotate within a predetermined range. Therefore, the terahertz wave incident to the scanning mirror 120 may be rapidly reflected within a predetermined angle range and be scanned to the scanning collimating module 130. At this time, the scanning mirror 120 may rotate in a single axis direction so that the terahertz wave may be scanned in a single axis direction.

Preferably, the scanning mirror 120 may be implemented using a Galvano mirror, a MEMS micro mirror or a Polygon mirror. Such mirrors may be suitably used as the scanning mirror 120 since the collimated light may be rapidly scanned within a predetermined angle range. However, various mirrors other than the above may also be adopted for the scanning mirror 120.

Meanwhile, the scanning mirror 120 may rotate in various ways. For example, in a case where a Galvano mirror is adopted as the scanning mirror 120, a current having a spherical wave or sine wave of a regular frequency is applied to the motor of the Galvano mirror, to obtain a desired repeated rotation of the Galvano mirror. Here, the rotating speed of the scanning mirror 120 may be 60 Hz to 100 Hz.

Meanwhile, the rotation angle, operation or speed of the scanning mirror 120 may be controlled by feed-back according to information collected by the terahertz wave detecting unit 400.

The scanning collimating module 130 collimates the terahertz waves reflected by the scanning mirror 120. In other words, if the scanning mirror 120 scans terahertz waves in a predetermined angle range, the scanning collimating module 130 reflects the scanned terahertz waves to be parallel and incident to the focusing lens 200 of the rotating plate 300.

Preferably, the scanning collimating module 130 may be implemented by a parabolic mirror. At this time, in a case where the terahertz wave supplying module 110 includes the beam collimating unit 113 and the beam collimating unit 113 is implemented using an off-axis parabolic mirror, the off-axis parabolic mirror of the scanning collimating module 130 may have a greater caliber than the off-axis parabolic mirror of the beam collimating unit 113. For example, the off-axis parabolic mirror for implementing the scanning collimating module 130 may have a caliber of 200 mm. Therefore, in a relative viewpoint, the off-axis parabolic mirror of the scanning collimating module 130 may be regarded as a large-caliber off-axis parabolic mirror, and the off-axis parabolic mirror of the beam collimating unit 113 may be regarded as a small-caliber off-axis parabolic mirror.

Here, the focus of the large-caliber off-axis parabolic mirror may be matched with the rotary shaft of the scanning mirror 120. In this case, the terahertz waves sweep the large-caliber off-axis parabolic mirror and are reflected by the large-caliber off-axis parabolic mirror at a predetermined angle due to the rotation of the scanning mirror 120, and the reflected terahertz waves are parallel and incident to the focusing lens 200 of the rotary shaft, so that the focused terahertz waves are repeatedly scanned to the object to be inspected 10. At this time, the scanning collimating module 130 may allow the parallel-reflected terahertz wave to be perpendicularly incident to the rotating plate 300 as shown in FIG. 13.

As described above, the scanning collimating module 130 which may be implemented using a large-caliber off-axis parabolic mirror or the like may allow terahertz waves to be repeatedly scanned through the focusing lens 200 of the rotating plate 300 to the upper portion of the object to be inspected 10, together with the scanning mirror 120.

At this time, the scanning mirror 120 and the scanning collimating module 130 may allow terahertz waves to be scanned to the rotating plate 300 in the raster scanning method. Particularly, in the present disclosure, since the focusing lens 200 is provided at the rotating plate 300, all scanned terahertz waves may pass through the focusing lens 200, which may greatly improve the optical resolution.

Meanwhile, the terahertz wave detecting unit 400 may include a reflection detecting unit and a penetration detecting unit.

Here, the reflection detecting unit may collect and detect the terahertz wave reflected by the object to be inspected 10. Particularly, in a case where the terahertz wave supplied to the object to be inspected 10 is reflected along its incident path, the reflection detecting unit may detect the reflected terahertz wave. For example, if the terahertz wave is generated by the terahertz wave generating unit 111 and incident to the object to be inspected 10 through the optical focusing unit 112, the beam collimating unit 113, the scanning mirror 120, the scanning collimating module 130 and the focusing lens 200 of the rotating plate 300 as in the embodiment of FIG. 13, the terahertz wave may be reflected on the object to be inspected 10 and moves again through the focusing lens 200 of the rotating plate 300, the scanning collimating module 130, the scanning mirror 120, and the beam collimating unit 113. In addition, the reflected terahertz wave may be collected through the reflection detecting unit and used for inspecting the object.

The penetration detecting unit may collect and detect the terahertz wave which has passed through the object to be inspected 10. At this time, the penetration detecting unit may have a concave mirror and silicon lens. Here, if the terahertz waves incident to the object to be inspected 10 penetrate the object to be inspected 10, the concave mirror may reflect the penetrated terahertz waves. In addition, the silicon lens may focus the terahertz waves reflected by the concave lens. The silicon lens may be hemispherical lens. Moreover, the penetration detecting unit may have a Schottky diode to collect and detect terahertz waves.

In a case where the terahertz wave detecting unit 400 includes a reflection detecting unit and a penetration detecting unit as in this embodiment, both the terahertz wave reflected by the object to be inspected 10 and the terahertz wave penetrating the object to be inspected 10 may be detected. Therefore, since both a reflection method and a penetration method are used when inspecting an object by using terahertz waves, various kinds of objects may be inspected regardless of materials or kinds of the object to be inspected 10.

However, such a configuration of the reflection detecting unit and the penetration detecting unit is just an example, and the terahertz wave detecting unit 400 may be implemented in various ways.

Meanwhile, for the terahertz wave detecting unit 400 to detect both the terahertz wave reflected by the object to be inspected 10 and the penetrated terahertz wave, the terahertz wave incident to the object to be inspected 10 via the focusing lens 200 of the rotating plate 300 preferably has an incident angle perpendicular to the incident surface of the object to be inspected 10. In addition, the terahertz wave incident to the object to be inspected 10 via the focusing lens 200 of the rotating plate 300 is preferably as parallel as possible. If the terahertz waves incident to the object to be inspected 10 are parallel as above, it will be easier to obtain a resolution with a shorter wavelength.

Preferably, the object inspection apparatus according to the present disclosure may further include a display unit 500, as shown in FIG. 1.

The display unit 500 may provide an image by using the terahertz wave detected by the terahertz wave detecting unit 400. For this, the display unit 500 may be connected to the terahertz wave detecting unit 400 and transmit/receive information to/from the terahertz wave detecting unit 400.

The display unit 500 may include a pre-amplifier, a lock-in amplifier, an A-D converter and a signal processing unit. In this case, the terahertz wave detected by the terahertz wave detecting unit 400 may be amplified through the pre-amplifier and the lock-in amplifier, A-D converted, and then transmitted to the signal processing unit. In this case, the signal processing unit may change the transmitted signal into a pixel value matching with an image coordinate by means of software and display a 2D image or the like on a monitor or the like. Therefore, a user may accurately and rapidly inspect an object by observing the displayed 2D image or the like.

Also preferably, the object inspection apparatus according to the present disclosure may further include a controller.

The controller may control each component of the object inspection apparatus. For example, when the signal processing unit of the display unit 500 of this embodiment displays the inspection result as a 2D image by using the terahertz wave detected by the terahertz wave detecting unit 400, the information notifying whether the terahertz wave detected by the terahertz wave detecting unit 400 may be appropriate to be displayed as a 2D image may be received from the signal processing unit. In this case, if the information notifying that the terahertz wave detected by the terahertz wave detecting unit 400 is not appropriate to be displayed as a 2D image is received from the signal processing unit, the controller may suitably change a rotation angle, speed or the like of the scanning mirror 120. As another example, the controller may control a rotating speed of the rotating plate 300 and/or a terahertz wave supplying speed of the terahertz wave supplying unit 100 in order to synchronize the rotation of the rotating plate 300 with the path movement of the terahertz wave supplying unit 100.

Also preferably, the object inspection apparatus according to the present disclosure may further include an object transfer unit 600 as shown in FIG. 1.

The object transfer unit 600 may transfer the object to be inspected 10. Particularly, the object transfer unit 600 may transfer the object to be inspected 10 in a direction perpendicular to the scanning direction of the terahertz wave supplying unit 100. For example, in a case where the terahertz wave supplying unit 100 supplies terahertz waves while moving their path in the x-axis direction, the object transfer unit 600 may transfer the object to be inspected 10 in the y-axis direction. In this embodiment, even though terahertz waves are scanned only in a single axis direction by the terahertz wave supplying unit 100, the terahertz waves may be scanned to the entire area of the object to be inspected 10 by moving the object to be inspected 10.

Figure 14:
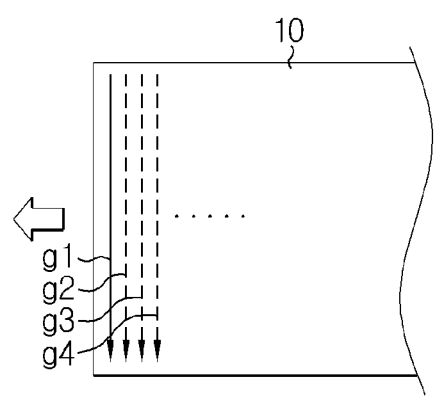
FIG. 14 is a top view schematically showing a configuration where a terahertz wave is scanned to an object to be inspected, which is transferred by an object transfer unit according to an embodiment of the present disclosure.

FIG. 14 is a top view schematically showing a configuration where a terahertz wave is scanned to an object to be inspected 10, which is transferred by the object transfer unit 600 according to an embodiment of the present disclosure.

Referring to FIG. 14, the object to be inspected 10 may be transferred from right to left by the object transfer unit 600. In addition, in this case, the terahertz wave supplying unit 100 may scan terahertz waves in the vertical direction on the figure to be perpendicular to the transferring direction of the object to be inspected 10. At this time, the terahertz wave supplying unit 100 scans terahertz waves while reciprocating in a beeline distance within the same area. However, since the object to be inspected 10 is transferred to the left direction by the object transfer unit 600, from the viewpoint of the object to be inspected 10, terahertz waves may be scanned while changing their locations as indicated by the arrows g1 to g4. In other words, even though the terahertz wave supplying unit 100 supplies terahertz waves only in a single axis direction, terahertz waves may be scanned to the entire surface of the object to be inspected 10 since the object to be inspected 10 is transferred by the object transfer unit 600. Therefore, if the above method is used, since 2D scanning for the object to be inspected 10 may be performed by means of just single axis scanning, a 2D image of the object to be inspected 10 may be obtained.

Meanwhile, even though FIG. 14 illustrates that terahertz waves are scanned only in a single direction, namely from top to bottom, by the terahertz wave supplying unit 100, it is just an example, and the present disclosure is not limited to such a scanning manner. For example, the terahertz wave supplying unit 100 may scan terahertz waves in both directions, namely from top to bottom or from bottom to top.

The object transfer unit 600 may be implemented using a conveyor belt. Particular, the object transfer unit 600 may include two conveyor belts successively arranged to transfer the object to be inspected 10 in a single axis direction. In this case, the terahertz waves supplied by the terahertz wave supplying unit 100 and focused through the focusing lens 200 of the rotating plate 300 may be scanned between two conveyor belts. In other words, the focused terahertz waves may be scanned to the object to be inspected 10 located between two conveyor belts. In this embodiment, the terahertz wave which has passed through the object to be inspected 10 may be detected without an interruption of the conveyor belt.

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

Meanwhile, even though the terms "unit" and "module" used herein, for example 'terahertz wave supplying unit', 'display unit', 'object transfer unit', 'terahertz wave supplying module', 'scanning collimating module', 'terahertz wave generating unit', 'optical focusing unit', 'beam collimating unit' or the like have been used herein, such terms represent a logical configuration unit, which do not represent an element that can be or must be physically divided, as apparent to those having ordinary skill in the art.

What is claimed is:

1. An object inspection apparatus, comprising:
a terahertz wave supplying unit for generating a terahertz wave and moving a path of the terahertz wave according to time so that the terahertz wave is supplied to an object to be inspected;
a focusing lens located between the terahertz wave supplying unit and the object to be inspected so that the terahertz wave supplied by the terahertz wave supplying unit is focused;
a rotating plate having a plate shape and including a plurality of the focusing lenses with different distances from the center thereof, the rotating plate rotating in the circumferential direction so that one of the focusing lenses is located at a path of the terahertz wave according to the path movement of the terahertz wave; and
a terahertz wave detecting unit for collecting and detecting a terahertz wave incident to the object to be inspected;
wherein the focusing lens includes a plurality of circular grooves formed at the rotating plate and having a same center and different radiuses so that the circular grooves are spaced apart from each other by a predetermined distance.

2. The object inspection apparatus according to claim 1, wherein the plurality of focusing lenses included in the rotating plate are arranged in a spiral pattern.

3. The object inspection apparatus according to claim 2, wherein the spiral pattern has at least two turns at the rotating plate.

4. The object inspection apparatus according to claim 1, wherein the rotating plate is synchronized as it rotates with the path movement of the terahertz wave.

5. The object inspection apparatus according to claim 1, wherein the grooves of the focusing lens are formed so that the thickness of the rotating plate decreases by a regular depth.

6. The object inspection apparatus according to claim 5, wherein the radiuses of the grooves of the focusing lens are determined according to the equation below:

$$r_n = \sqrt{n\lambda f + \frac{n^2\lambda^2}{4}}$$

where r represents a radius of each groove, n is a natural number and represents an order from the center of the grooves, λ represents a wavelength of the terahertz wave, and f represents a focal distance.

7. The object inspection apparatus according to claim 1, wherein the focusing lens is made of an optically transparent material in a terahertz wave region.

8. The object inspection apparatus according to claim 1, wherein the terahertz wave supplying unit moves the path of the terahertz wave in a straight line.

9. The object inspection apparatus according to claim 1, wherein the terahertz wave supplying unit includes:
a terahertz wave supplying module for generating and supplying a terahertz wave;
a scanning mirror for rapidly reflecting the terahertz wave, supplied by the terahertz wave supplying module, in a predetermined angle range while rotating; and
a scanning collimating module for collimating the terahertz wave reflected by the scanning mirror so that the parallel terahertz wave is incident on an object to be inspected.

10. The object inspection apparatus according to claim 9, wherein the terahertz wave supplying module includes:
a terahertz wave generating unit for generating and emitting a terahertz wave;
an optical focusing unit for focusing the terahertz wave, emitted from the terahertz wave generating unit, to have a reduced field angle; and
a beam collimating unit for collimating the terahertz wave focused by the optical focusing unit.

11. The object inspection apparatus according to claim 1, wherein the terahertz wave detecting unit includes:
a reflection detecting unit for detecting the terahertz wave reflected by the object to be inspected; and
a penetration detecting unit for detecting the terahertz wave penetrating through the object to be inspected.

12. The object inspection apparatus according to claim 1, further comprising a display unit for providing an image by using the terahertz wave detected by the terahertz wave detecting unit.

13. The object inspection apparatus according to claim 1, further comprising an object transfer unit for transferring the object to be inspected.

14. The object inspection apparatus according to claim 13, wherein the object transfer unit includes two conveyor belts arranged sequentially to transfer the object to be inspected, and the terahertz wave focused by the focusing lens is incident between the two conveyor belts.

15. A focusing lens for focusing a terahertz wave, wherein a plurality of circular grooves having the same center and different radiuses are formed at the focusing lens so that the circular grooves are spaced apart from each other by a predetermined distance.

16. The focusing lens according to claim 15, wherein the plurality of circular grooves are formed so that the thickness of the rotating plate decreases by a regular depth.

17. The focusing lens according to claim 16, wherein the radiuses of the grooves of the focusing lens are determined according to the equation below:

$$r_n = \sqrt{n\lambda f + \frac{n^2\lambda^2}{4}}$$

where r represents a radius of each groove, n is a natural number and represents an order from the center of the grooves, λ represents a wavelength of the terahertz wave, and f represents a focal distance.

18. The focusing lens according to claim 15, wherein the focusing lens is made of an optically transparent material in a terahertz wave region.

* * * * *